United States Patent
Han et al.

(10) Patent No.: US 9,006,490 B2
(45) Date of Patent: Apr. 14, 2015

(54) METHOD FOR DIRECT FUNCTIONALIZATION OF POLYANILINE AND OTHER MOLECULES HAVING DIIMINOQUINOID RING VIA C-C BOND FORMATION

(75) Inventors: Chien-Chung Han, Hsinchu (TW); Hong-Pin Shih, Hsinchu (TW)

(73) Assignee: Chien-Chung Han, Hsinchu (TW)

( * ) Notice: Subject to any disclaimer, the term of this patent is extended or adjusted under 35 U.S.C. 154(b) by 711 days.

(21) Appl. No.: 12/953,361

(22) Filed: Nov. 23, 2010

(65) Prior Publication Data

US 2012/0130114 A1 May 24, 2012

(51) Int. Cl.
*C07C 211/00* (2006.01)
*C07C 209/52* (2006.01)
*C07C 221/00* (2006.01)
*C07C 253/30* (2006.01)

(52) U.S. Cl.
CPC ............. *C07C 209/52* (2013.01); *C07C 221/00* (2013.01); *C07C 253/30* (2013.01)

(58) Field of Classification Search
USPC ........................................................ 564/433
See application file for complete search history.

(56) References Cited

U.S. PATENT DOCUMENTS 6,380,346 B1 4/2002 Han
7,034,100 B2 4/2006 Han
7,273,918 B2 9/2007 Han et al.

OTHER PUBLICATIONS

Johnson et al., J. Med. Chem., (1981) 24, 1314-1319.*
Taimr et al., Die Angewandte Makromolekulare Chemie 169 (1989) 37-48.*
Han et al. Org. Biomol. Chem., 4, (2006) 3511-3516.*
Velikorodov et al Russian Journal of Organic Chemistry, 46(7) (2010) 1060-1065.*
Paike et al., "A Serendipitous C-C Bond Formation Reaction between Michael Donors and Diiminoquinoid Ring Assisted by Quaternary Ammonium Fluoride", Organic Letters, 2009, vol. 11, No. 24, pp. 5586-5589.

* cited by examiner

*Primary Examiner* — Nyeemah A Grazier
(74) *Attorney, Agent, or Firm* — Jianq Chyun IP Office

(57) ABSTRACT

A method for direct functionalization of polyaniline and other molecules with at least one diiminoquinoid ring through C—C bond formation is described. Fluoride ion, or a weak base whose conjugated acid form has a $pK_a$ value of 1-10, is used as a catalyst to react the molecule with an organic compound that has an abstractable proton directly bonded to the target carbon atom thereof to be bonded to the diiminoquinoid ring and has a pKa value less than 30 for the abstractable proton.

8 Claims, No Drawings

METHOD FOR DIRECT FUNCTIONALIZATION OF POLYANILINE AND OTHER MOLECULES HAVING DIIMINOQUINOID RING VIA C-C BOND FORMATION

BACKGROUND OF THE INVENTION

1. Field of Invention

The invention relates to a method for direct functionalization of polyaniline and other molecules having at least one diiminoquinoid ring through C—C bond formation, and to a product yielded with the same method.

2. Description of Related Art

Addition reactions for the α,β-unsaturated carbonyl compounds via Michael addition reaction through the formation of a new C—C bond have been reported. While the similar Michael addition reactions for the α,β-unsaturated imino compounds or diiminoquinoid rings through the formation of a new C—C bond have not been successfully prepared and reported. Pan is known to be an important type of conducting polymer, which has diaminobenzenoid rings and diiminoquinoid rings in a certain ratio and has been renowned for its poor solution-processability in the absence of substituents on the rings.

Though the solubilities of substituted-polyanilines (S-Pans) prepared from alkyl- and alkoxy-substituted aniline monomers via the conventional oxidative polymerization or copolymerization method were found to be higher than the unsubstituted Pan, their conductivities were found to be ~1-5 orders of magnitude lower than the unsubstituted Pan. The much reduced conductivities are believed to be caused by the increased extent of the non-conjugated defect backbone structures that was induced to form during the growth of the polymer chain due to the competing electronic directing placement effect of the substituent.

Such problem can be solved by using the concurrent reduction and substitution (CRS) reaction method to introduce substituents after the polyaniline backbone is made. For example, highly conductive and highly processable functionalized polyanilines with various alkylthio or alkylamino groups have been prepared via the CRS method by reacting a Pan of a desirable redox state with thiols or amines as nucleophiles. The reactions were believed to occur at the diiminoquinoid sites following a typical Michael addition fashion, which converted unsubstituted diiminoquinoid rings into substituted diaminobenzenoid rings, via the formation of a new C—S or C—N bond, respectively.

Although these alkylthio- and alkylamino-substituted polyanilines all showed clearly improved processability, they still suffered some disadvantages. For example, the alkylamino-substituted polyanilines in general show an order of magnitude lower conductivity than the unsubstituted-Pan, due to the fact that these newly introduced amino groups have relative higher basicities and would compete significantly with the polyaniline backbone for the protonic acid dopant, thus showing an adverse effect on the conductivity for the doped Pan. Although the alkylthio-substituted polyanilines do not show such adverse conductivity effect, the relative weak C—S bond and the oxidation-sensitive sulfide group would render the materials and possibly their application products with relative poor long-term stabilities. Thus, it would be highly desirable to functionalize Pan with an alkyl group via the CRS reaction route, because the alkyl group is not only less basic than an amino group, but also more stable against oxidation than an alkylthio group.

However, the efforts in extending the same addition reaction to carbon-based nucleophiles have however proved to be futile, up to now.

SUMMARY OF THE INVENTION

Accordingly, this invention provides a method for direct functionalization of polyaniline and other molecules with at least one diiminoquinoid ring through C—C bond formation.

This invention also provides a product yielded with the above method.

The method for directly functionalizing polyaniline and other molecules with at least one diiminoquinoid ring through C—C bond formation of this invention is described as follows. Fluoride ion, or a weak base whose conjugated acid form has a $pK_a$ value of 1-10, is used as a catalyst to react the polyaniline or the molecule with an organic compound that has an abstractable proton directly bonded to the target carbon atom thereof to be bonded to the diiminoquinoid ring and has a pKa value less than 30 for the abstractable proton.

The pKa value for the abstractable proton is preferably less than 20 and more preferably less than 15. The weak base preferably includes a nitrogen-containing base whose conjugated acid form has a $pK_a$ value of 2-9, and more preferably includes a base whose conjugated acid form has a $pK_a$ value of 3-8.

The above molecule may be a small molecule or a substituted or unsubstituted polyaniline (Pan) molecule, having at least one unit of diiminoquinoid ring in their molecular frameworks.

In an embodiment, the organic compound is expressed by the following formula:

(4)

In formula (4), $R^1$, $R^2$ and $R^3$ are selected from the group consisting of hydrogen, alkyl, alkoxy, aryl, heteroaryl and electron-withdrawing groups, with the proviso that at least one of $R^1$, $R^2$ and $R^3$ represents an electron-withdrawing group; and any two of $R^1$, $R^2$ and $R^3$ may join together to form a ring with the target carbon atom.

The product yielded with the above method of this invention may be a small molecule or a polyaniline (Pan) molecule being substituted on the ring with the —$CR^1R^2R^3$ group or a group further derived from the initial attached —$CR^1R^2R^3$ group.

The substituted polyanilines with substituents bonded to the backbone through carbon atoms also have improved solubilities and/or enhanced functionalitiy without suffering a significant adverse effect on the conductivities.

In order to make the aforementioned and other objects, features and advantages of this invention comprehensible, a preferred embodiment is described in detail below.

DESCRIPTION OF EMBODIMENTS

The method for direct functionalization of polyaniline and other molecules with at least one diiminoquinoid ring through C—C bond formation of this invention can be applied to a small molecule expressed by formula (1), or an unsubstituted polyaniline or a substituted polyaniline molecule as expressed by formula (2) and (3), respectively:

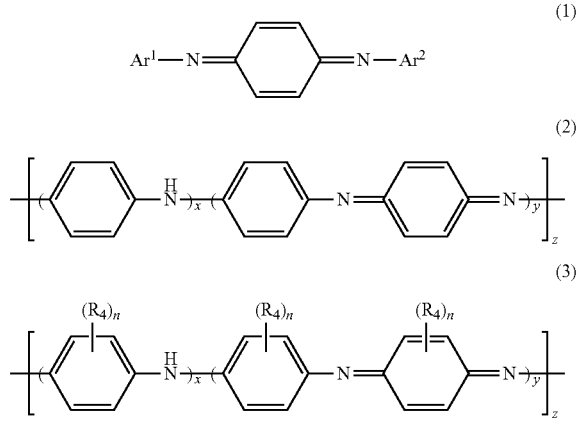

(1)

(2)

(3)

or unsubstituted aniline monomers through chemical or electrochemical oxidative polymerization or copolymerization.

The organic compound to be reacted with the diiminoquinoid ring-containing molecule features with an abstractable proton on a carbon atom having a pKa value less than 30 for the abstractable proton. The pKa value is preferably less than 20, and more preferably less than 15.

Taking the small molecule expressed by formula (1) as an example, the proposed mechanism for the C—C bond forming reaction is shown in Scheme 1 below, wherein the organic compound as a reactant with an abstractable proton directly bonded to the carbon atom to be bonded to the ring is expressed by R*H. The mechanism of the reaction of the Pan molecule of formulae (2) and (3) having multiple diiminoquinoid rings is similar. It is noted that the protonation could also occur at the N—$Ar^1$ side and render the R* to be bonded to the carbon atom near the N—$Ar^2$ side.

Scheme 1: Plausible mechanism for a molecule with one diiminoquinoid ring.

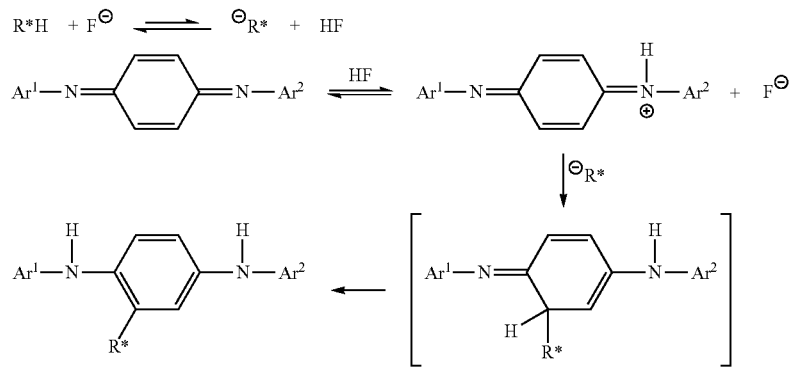

In formula (1), each of $Ar^1$ and $Ar^2$ represents substituted or unsubstituted aryl and heteroaryl groups, providing that they can help stabilize the intermediate iminium ion formed during the C—C bond forming reaction assisted by the fluoride ion or other effective weak base. The carbon number of the aryl or heteroaryl group may be equal to or greater than two. When $Ar^1$ and $Ar^2$ are both phenyl, the compound of formula (1) is denominated as N,N'-diphenyl-1,4-phenylenediimine (PDI).

In formula (2) and (3), x is an integer equal to or greater than 0, y is an integer equal to or greater than 1, z is an integer equal to or greater than 1, and n is the same or different at each occurrence and ranges from 0 to 3 with a proviso that at least one of n in the polyaniline backbone is nonzero. In addition, x and y are the same or different at each occurrence, and z usually ranges from 1 to $10^8$. $R^4$'s are the same or different at each occurrence and can be selected from alkyl, aryl, heteroaryl, alkoxy, allyl, benzyl, alkoxy, aryloxy, cycloalkyl, alkanoyl, aryloyl, aryloyloxy, alkanoyloxy, alkylthio, arylthio, halo, hydroxyl, cyano, nitro, alkylsilyl, arylsilyl, amino, acid, and epoxy moieties. The polyaniline molecule, before its use for the functionalization reaction, may be first subjected to a redox treatment to form the desirable redox state having a desirable number of the oxidized repeat units containing the diiminoquinoid rings, wherein the starting polyaniline material can be synthesized from the substituted In general, the above organic compound can be expressed by formula (4):

(4)

In formula (4), the group —$CR^1R^2R^3$ corresponds to the above group R*, wherein $R^1$, $R^2$ and $R^3$ are selected from the group consisting of hydrogen, alkyl, alkoxy, aryl, heteroaryl and electron-withdrawing groups, with the proviso that at least one of $R^1$, $R^2$ and $R^3$ represents an electron-withdrawing group; and any two of $R^1$, $R^2$ and $R^3$ may join together to form a ring with the target carbon atom. The criterion on having at least one electron-withdrawing group in formula (4) is intended to render the abstractable proton with a pKa value of less than 30 so that the addition reaction can effectively take place.

After reacting with organic compound (4), the product yielded from the small molecule (1) or from the Pan molecules (2) and (3) can be expressed by the following formula (5), (6), and (7), respectively.

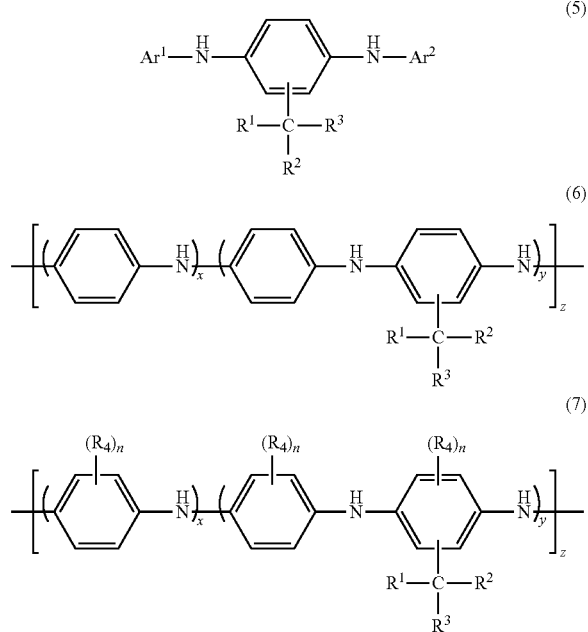

In formulae (5), (6), and (7), $Ar^1$, $Ar^2$, x, y, z, n, $R^1$, $R^2$, $R^3$ and $R^4$ are defined as above.

The electron-withdrawing group of $R^1$, $R^2$, and $R^3$ in compound (4) is selected from oxygen-containing electron-withdrawing groups, nitrogen-containing electron-withdrawing groups, sulfur-containing electron-withdrawing groups, phosphorous-containing electron-withdrawing groups, electron-withdrawing aromatic and heteroaromatic groups, α-haloalkyl groups, and halogen atoms.

Examples of the oxygen-containing electron-withdrawing groups include [—C(=O)$R^5$], wherein $R^5$ is selected from hydrogen, alkyl, aryl, heteroaryl, alkoxy, aryloxy, heteroaryloxy, alkylthio, arylthio, heteroarylthio, amino, alkylamino, dialkylamino, arylamino, diarylamino, alkylarylamino, and hydroxyl groups.

Examples of the nitrogen-containing electron-withdrawing groups include cyano, nitro, and —C(=N—$R^6$)$R^7$, wherein $R^6$ and $R^7$ are the same or different in each occurrence and is selected from hydrogen, alkyl, aryl, and heteroaryl groups.

Examples of the sulfur-containing electron-withdrawing groups include —S(=O)$R^8$ and —S(=O)$_2R^9$. $R^8$ and $R^9$ are the same or different at each occurrence and is selected from hydrogen, alkyl, aryl, heteroaryl, alkoxy, aryloxy, heteroaryloxy, amino, alkylamino, dialkylamino, arylamino, diarylamino, alkylarylamino, and hydroxyl groups.

Examples of the phosphorous-containing electron-withdrawing groups include —P(=O)$R^{10}R^{11}$ and —P(=O)$_2R^{12}$. $R^{10}$, $R^{11}$ and $R^{12}$ is the same or different and is selected from hydrogen, alkyl, aryl, heteroaryl, alkoxy, aryloxy, heteroaryloxy, alkylthio, arylthio, heteroarylthio, amino, alkylamino, dialkylamino, arylamino, diarylamino, alkylarylamino, and hydroxyl groups.

Examples of the electron-withdrawing aromatic groups include aryl rings having one or more electron-withdrawing groups, and electron-withdrawing heteroaryl groups. Examples of the aryl rings having one or more electron-withdrawing groups include —$CF_3$-substituted aryl, $NO_2$-substituted aryl, carbonyl-substituted aryl, halogen-substituted aryl, and cyano-substituted aryl. Examples of the electron-withdrawing heteroaryl groups include the substituent ring derived from pyridine, pyrimidine, imidazole, purine, adenine, guanine, cytosine, uracil, thymine, and histidine.

Regarding the proviso that at least one of $R^1$, $R^2$ and $R^3$ represents an electron-withdrawing group, it is possible that only one electron-withdrawing group is sufficient to render the α-hydrogen with a pKa value less than 30, 20 or 15. For example, $CH_3CN$ has a pKa value of 25, $CH_3CHO$ has a pKa value of 17, and $CH_3NO_2$ has a pKa value of 10.2.

It is also possible that two or three electron-withdrawing groups together render the α-hydrogen with an even smaller pKa value. In the cases of two electron-withdrawing groups, e.g., acetylacetone (acac) has a pKa value of 8.9, and dicyanomethane has a pKa of ~11.

It is also possible that a single electron-withdrawing group alone is not sufficient to render the α-hydrogen with a pKa value less than 30 but two or three such electron-withdrawing groups work together can achieve so.

Moreover, when two of $R^1$, $R^2$ and $R^3$ join together to form a ring with the target carbon atom, the ring may include at last one electron-withdrawing group, or include no electron-withdrawing group. In an example of the former case, two of $R^1$, $R^2$ and $R^3$ and the target carbon atom together form a 5- or 6-membered carbon ring with two carbonyl or imino groups at the 2- and 5-positions or the 2- and 6-positions. For example, cyclopentane-2,5-dione has a pKa value of about 8-9. In the latter case, examples of the divalent groups constituted by the two of $R^1$, $R^2$ and $R^3$ that form a ring with the target carbon atom include $C_{4-6}$ alkylene.

The effective catalyst is selected from fluoride and a weak base whose conjugated acid form has a $pK_a$ value of 1-10. Preferably, the base includes a nitrogen-containing base whose conjugated acid form has a $pK_a$ value of 2-9. More preferably, the said conjugated acid form has a $pK_a$ value of 3-8. Examples of the nitrogen-containing weak base include substituted and unsubstituted anilines, N-substituted anilines, PDI, oligomeric anilines, phenyl-caped oligomeric anilines, and polyanilines; substituted and unsubstituted pyridines, pyrimidines, imidazoles, purines, adenines, guanines, and histidines.

Further, the presence of these newly introduced functional groups bonded to the polyaniline backbone or the product therewith through carbon atoms and having the electron withdrawing moiety, such as carbonyl, imine, phosphine oxide, sulfoxide, sulfone and cyano groups, can greatly enhance the anchoring ability of the conjugated molecules to the surface of $TiO_2$ nano-particles used in a dye-sensitized solar cell device, thus enabling their application as an organic dye for a solar cell device.

EXAMPLES

The following examples are provided to further describe this invention, which are however not intended to limit the scope of this invention.

Comparative Examples 1-7 & Examples 1-6

In Comparative Examples (abbreviated to "CEx.") 1-7 and Examples ("Ex.") 1-6, a certain amount of the starting material PDI was dissolved in different solvents with different amounts [in the unit of "equivalent" ("equiv.")] of TBAF and reacted under different conditions, as shown in Table 1. The organic compound to be reacted with the starting material PDI is the solvent in CEx. 1-7 and Ex. 1-2. The results of these examples are also shown in Table 1.

TABLE 1

| Entry[a] | TBAF (equiv.) | Solvent | Yield[c] (%) |
|---|---|---|---|
| CEx. 1 | 4 | MeOH | N.R. |
| CEx. 2 | 4 | CH$_3$CN | N.R. |
| CEx. 3 | 4 | CH$_2$Cl$_2$ | N.R. |
| CEx. 4 | 4 | DMSO | N.R. |
| CEx. 5 | 4 | DMF | N.R. |
| CEx. 6 | 4 | THF | N.R. |
| CEx. 7 | 0 | CH$_3$NO$_2$ | N.R. |
| Ex. 1 | 4 | CH$_3$NO$_2$ | 71 |
| Ex. 2 | 4 | CH$_3$NO$_2$ | 73 |
| Ex. 3 | 4 | CH$_3$CN[b] | 72 |
| Ex. 4 | 2 | CH$_3$CN[b] | 70 |
| Ex. 5 | 1 | CH$_3$CN[b] | 68 |
| Ex. 6 | 0.5 | CH$_3$CN[b] | 65 |

[a]Reaction conditions: room temperature for 15 h for CEx. 1-7 and Ex. 1; 70° C. for 45 min for Ex. 2-6.
[b]Containing 1 vol % of CH$_3$NO$_2$.
[c]Yield of isolated product after column chromatography; N.R.: no reaction.

In Example 1, the reaction was conducted at room temperature, all the starting material PDI was found to be consumed within 15 h. During the reaction course, the color of the reaction solution changed gradually from orange to pale yellow, indicating the gradual disappearance of PDI. At higher reaction temperature (70 C, Ex. 2), the same reaction proceeded much faster and finished within 45 min, as shown in Table 1.

The $^1$H NMR spectrum of the product showed the typical spectrum for a mono-substituted N,N'-diphenyl-1,4-phenylene-diamine (mono-PDA) with the substituent at the central ring, while both of its $^1$H and $^{13}$C NMR spectra showed no $^1$H-$^{19}$F splitting pattern. Instead, the $^1$H NMR of the product showed the presence of an extra singlet peak at ~δ 5.5, which did not undergo H-D exchange as D$_2$O was added. The peak integration indicated that the new singlet accounts for methylene protons, which was also confirmed by $^{13}$C DEPT and 2D NMR (e.g., HMBC, HSQC) study. The HRMS data indicated that it is a PDA being mono-substituted by a moiety having a mass of 60, corresponding to a —CH$_2$NO$_2$ group instead of a fluorine atom.

According to CEx. 7, the control experiment indicated that no reaction occurred between PDI and CH$_3$NO$_2$ in absence of TBAF, which clearly showed that TBAF was mediating the reaction.

Moreover, according to Ex. 3-6, the addition reaction can proceed under similar conditions even with CH$_3$NO$_2$ as low as 1 vol % in other solvent mediums like CH$_3$CN, as well as with a lesser amount of catalyst (TBAF, 0.5-4 equiv.), giving quite similar yields. The significance of this reaction was shown by the fact that when the CRS reaction was tried between PDI and n-BuLi, there was no sign for the formation of butyl-substituted PDA, even when CH$_3$NO$_2$ was used as a solvent. Other bases (e.g., KOH, NaOH, NEt$_3$ or DBU) in CH$_3$NO$_2$ have also failed to promote the reaction. The tetrabutylammonium salts with a counter anion having a stronger nucleophilicity, such as tetrabutylammonium chloride and tetrabutylammonium bromide, also failed.

Hence, it is evident that it is the fluoride anion of TBAF mediating the addition reaction to yield substituted PDA's. These results confirm the reaction mechanism as provided in the above Scheme 1. The mechanism of the reaction of CH$_3$NO$_2$ and PDI is shown in Scheme 2.

Scheme 2:

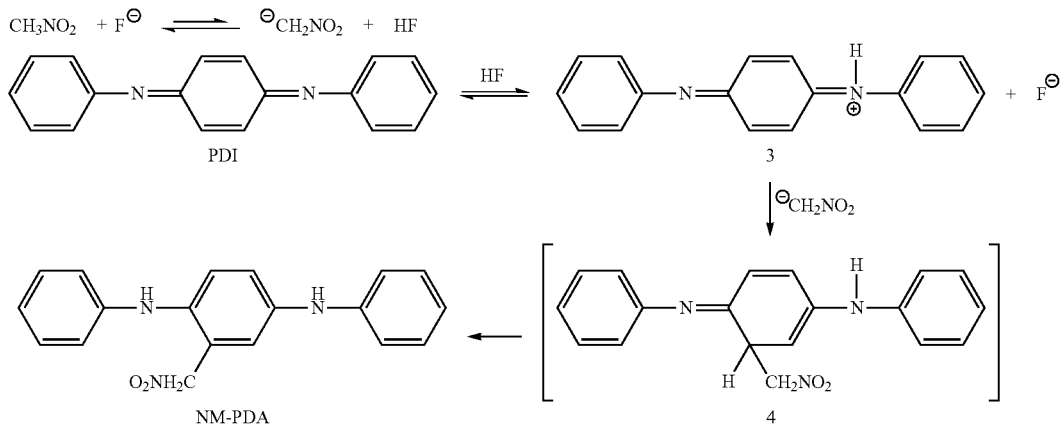

When the fluoride encounters the CH$_3$NO$_2$ molecule, a small equilibrium amount of HF and nitromethane anion is formed as driven by the strong bonding energy of H—F (136 kcal/mol) and the relatively low pKa value of nitromethane. Unlike MeOH, the released HF is acidic enough to protonate the N-atom of the imino of PDI and renders the diiminoquinoid ring 3 reactive enough to be nucleophilically attacked by the nitro-methane anion. The resultant nitromethylated intermediate 4 then undergoes either a 1,3-H shift or deprotonation and then a protonation process with the aid of fluoride as a base to yield the final nitromethylated-PDA (NM-PDA). The fluoride anion released from the above reaction cycle can induce another reaction cycle, which accounts for the catalytic nature of this reaction. The mechanism can also explain the ineffectiveness of tetrabutylammonium chloride/bromide, for the initial deprotonation of nitromethane by Cl$^-$ or Br$^-$ are much unlikely due to the much weaker bonding strength of HCl (103 kcal/mol) and HBr (88 kcal/mol).

Examples 7-13

More experiments were done using various other Michael donors, which include those with one electron-withdrawing group (nitro) and one or two electron-donating groups (methyl) (Ex. 7-8) and those with two electron-withdrawing groups each being selected from carbonyl, cyano and ester groups (Ex. 9-13 using diketones, keto esters, dicyano and cyano esters). The results are shown in Table 2, and the result of Ex. 3 is also shown for comparison.
TABLE 2
| Entry[a] | Michael donors | Time (min) | Product | Yield[b] (%) |
|---|---|---|---|---|
| Ex. 3 | $CH_3NO_2$ | 45 | 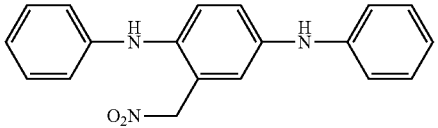<br>6a | 72 |
| Ex. 7 | 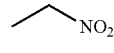 | 50 | 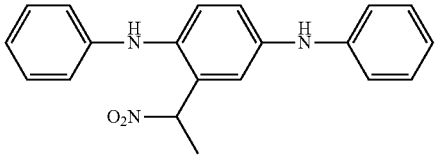<br>6b | 70 |
| Ex. 8 | 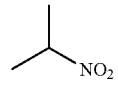 | 60 | 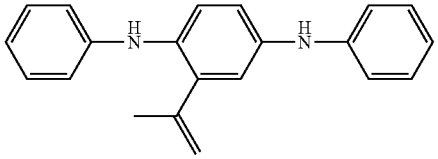<br>6c | 68 |
| Ex. 9 | 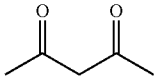 | 50 | 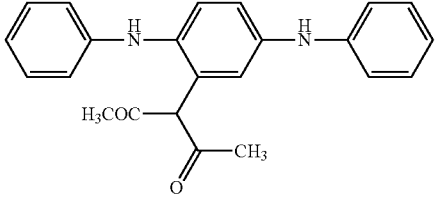<br>6d | 74 |
| Ex. 10 | 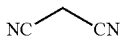 | 45 | 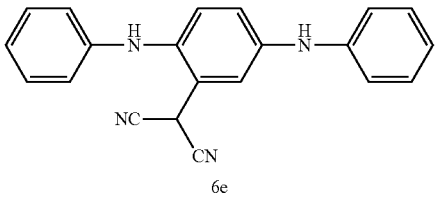 [SMILES: N#CC(C#N)c1cc(Nc2ccccc2)ccc1Nc1ccccc1]<br>6e | 80 |
| Ex. 11 | 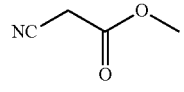 | 50 | 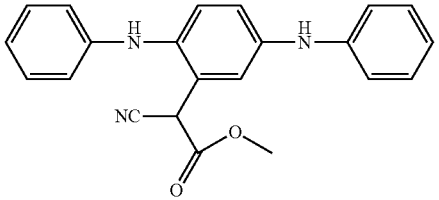<br>6f | 76 |
| Ex. 12 | 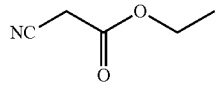 | 55 | 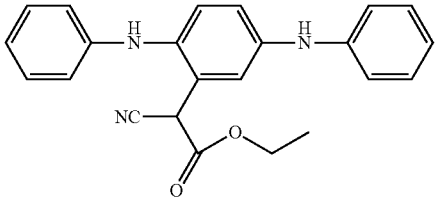<br>6g | 77 |

TABLE 2-continued

| Entry[a] | Michael donors | Time (min) | Product | Yield[b] (%) |
|---|---|---|---|---|
| Ex. 13 | 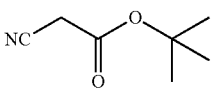 | 55 | 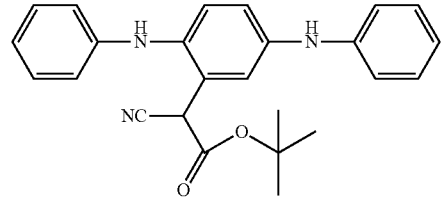 6h | 73 |

[a] All reactions were carried out at 70° C. in CH$_3$CN containing 1 vol % of Michael donor and 4 equiv. of TBAF.
[b] Yield of isolated product after column chromatography.

According to Ex. 7-8, it's known that the CRS reaction between PDI and Michael donors can tolerate both electron-donating and electron-withdrawing groups therein and give good isolated yield (68-80%) in a short span of reaction time (40-55 min) at 70 C in acetonitrile.

Also, according to Ex. 9-13, the Michael donors with two electron-withdrawing groups directly bonded to the target carbon atom worked very well and delivered desired compounds in good to excellent yield.

It is also noted that the $^1$H NMR spectra (in DMSO-d$_6$) of those compounds with a CN substituent (Ex. 10-13, Table 2) at the benzylic position however showed no peaks corresponding to benzylic C—H. Also, their $^1$H NMR spectra showed two different NH peaks, with one peak at about δ 5.9-6.6 accounting for two protons and another peak at about δ 6.5-7.9 for one proton (confirmed by H-D exchange experiments). Moreover, their $^{13}$C NMR spectra and their corresponding 2D NMR (e.g., HMBC, HSQC) studies confirmed that they all have a quarternary, but not a tertiary benzylic carbon.

It is rationalized that these compounds might have undergone further enolization due to the high acidity of the resultant benzylic protons and the basic nature of the NH group of the PDA backbone system, as driven by the energy gains from their enlarged conjugation extent and the additional H-bonding (or Coulombic) interaction.

Similar enolization has also occurred to the acetylacetonated-PDA (Ex. 9, Table 2), as evidenced by a missing benzylic proton and the formation of two different methyl groups. Interestingly, in the case of 2-nitropropane, it was found that the original nitro group at the benzylic position seems to undergo further elimination to yield a diamino-substituted α-methylstyrene. In the case of nitroethane, the product 6b is stable in its solid form at low temperature, but in solution state it gradually lost its HNO$_2$ group, forming a diamino-substituted styrene that readily underwent further polymerization, possibly being catalyzed by the released HNO$_2$ acid. To these low pKa Michael donor systems, the same reaction mechanism as illustrated in Scheme 2 might be applied.

These novel Michael addition reactions have also been successfully expanded to the polymer system, providing the first feasible synthetic method for a direct addition of a C-based substituent to the benzene rings of Pan and rendering the possible syntheses of various novel functionalized polyanilines (Scheme 3) for the first time.

Scheme 3. Preparation of Novel Functionalized Pans

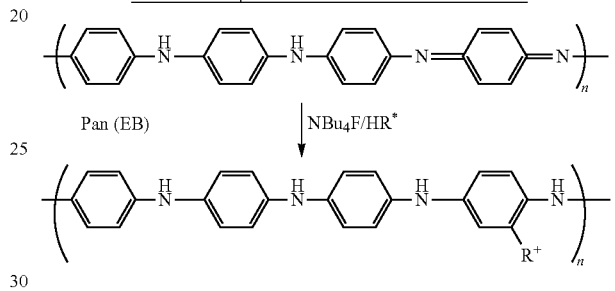

In another example, Pan powder was heated, in the absence of fluoride, at 70° C. with nitroethane that was used as both the solvent and the organic compound with an abstractable proton. The reaction, as monitored by the UV-vis spectrum of the sampled Pan during the reaction period, was found to reach completeness in about 24 h. On the other hand, if the same reaction was performed in the presence of 1 equivalent of NBu$_4$F catalyst under the same conditions, the reaction was found to reach completeness within 1 h. The results obtained in this example indicated that, in the absence of fluoride catalyst, Pan can serve as an effective weak base (whose conjugated acid form has a pKa value of 5-6) catalyst to enable the reaction between nitroethane and Pan to occur, even though it is not as effective as the fluoride catalyst.

The substituted polyanilines with substituents bonded to the backbone through carbon atoms according to the above embodiments and examples of this invention also have improved solubilities and/or enhanced functionalitiy without suffering a significant adverse effect on the conductivities.

This invention has been disclosed above in the preferred embodiments, but is not limited to those. It is known to persons skilled in the art that some modifications and innovations may be made without departing from the spirit and scope of this invention. Hence, the scope of this invention should be defined by the following claims.

What is claimed is:

1. A method for direct functionalization of a molecule having one or more diiminoquinoid rings through C—C bond formation, comprising:
   using fluoride ion, or a weak base whose conjugated acid form has a pK$_a$ value of 1-10, as a catalyst to react the molecule with an organic compound that has an abstractable proton directly bonded to a target carbon atom thereof to be bonded to the diiminoquinoid ring and has a pK$_a$ value less than 15 for the abstractable proton, wherein the organic compound is expressed by formula (4):

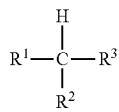
(4)

wherein
R$^1$, R$^2$ and R$^3$ are selected from the group consisting of hydrogen, alkyl, alkoxy, aryl, heteroaryl and electron-withdrawing groups, with a proviso that at least one of R$^1$, R$^2$ and R$^3$ represents an electron-withdrawing group, and
any two of R$^1$, R$^2$ and R$^3$ may join together to form a ring with the target carbon atom.

2. The method of claim 1, wherein the pK$_a$ value of the conjugated acid form of the weak base ranges from 3 to 8.

3. The method of claim 1, wherein the weak base comprises a nitrogen-containing base whose conjugated acid form has a pK$_a$ value of 2-9.

4. The method of claim 1, wherein the molecule is a small molecule expressed by formula (1):

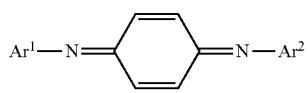
(1)

wherein each of Ar$^1$ and Ar$^2$ represents aryl or heteroaryl.

5. The method of claim 1, wherein the molecule is a polyaniline expressed by formula (2) or (3):

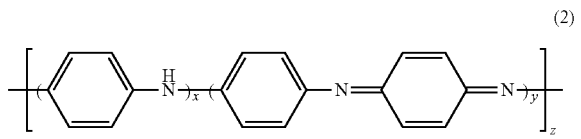
(2)

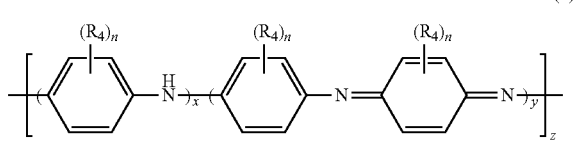
(3)

wherein x is an integer equal to or greater than 0, y is an integer equal to or greater than 1, z ranges from 1 to 10$^8$, n is the same or different at each occurrence and ranges from 0 to 3 with a proviso that at least one of n in the polyaniline backbone is nonzero, and R$^4$'s are the same or different at each occurrence and are selected from the group consisting of alkyl, aryl, heteroaryl, alkoxy, allyl, benzyl, aryloxy, cycloalkyl, alkanoyl, aryloyl, aryloyloxy, alkanoyloxy, alkylthio, arylthio, halo, hydroxyl, cyano, nitro, alkylsilyl, arylsilyl, amino, acid, and epoxy moieties.

6. The method of claim 1, wherein the electron-withdrawing groups are selected from the group consisting of oxygen-containing electron-withdrawing groups, nitrogen-containing electron-withdrawing groups, sulfur-containing electron-withdrawing groups, phosphorous-containing electron-withdrawing groups, electron-withdrawing aromatic groups, α-haloalkyl groups, and halogen atoms.

7. The method of claim 6, wherein
the oxygen-containing electron-withdrawing groups are represented by —C(=O)R$^5$, wherein R$^5$ is selected from the group consisting of hydrogen, alkyl, aryl, heteroaryl, alkoxy, aryloxy, heteroaryloxy, alkylthio, arylthio, heteroarylthio, amino, alkylamino, dialkylamino, arylamino, diarylamino, alkylarylamino, and hydroxyl groups;
the nitrogen-containing electron-withdrawing groups are selected from the group consisting of cyano, nitro, and —C(=N—R$^6$)R$^7$, wherein R$^6$ and R$^7$ are the same or different at each occurrence and are selected from the group consisting of hydrogen, alkyl, aryl and heteroaryl groups;
the sulfur-containing electron-withdrawing groups are selected from the group consisting of —S(=O)R$^8$ and —S(=O)$_2$R$^9$, wherein R$^8$ and R$^9$ are the same or different at each occurrence and are selected from the group consisting of hydrogen, alkyl, aryl, heteroaryl, alkoxy, aryloxy, heteroaryloxy, amino, alkylamino, dialkylamino, arylamino, diarylamino, alkylarylamino, and hydroxyl groups;
the phosphorous-containing electron-withdrawing groups are selected from the group consisting of —P(=O)R$^{10}$R$^{11}$ and —P(=O)$_2$R$^{12}$, wherein R$^{10}$, R$^{11}$ and R$^{12}$ are the same or different at each occurrence and are selected from the group consisting of hydrogen, alkyl, aryl, heteroaryl, alkoxy, aryloxy, heteroaryloxy, alkylthio, arylthio, heteroarylthio, amino, alkylamino, dialkylamino, arylamino, diarylamino, alkylarylamino, and hydroxyl groups; and
the electron-withdrawing aromatic groups are selected from the group consisting of aryl rings having one or more electron-withdrawing groups, and electron-withdrawing heteroaryl group.

8. The method of claim 1, wherein the one diiminoquinoid ring or each of the diiminoquinoid rings is bonded between aromatic rings.

* * * * *